US008478419B2

(12) United States Patent
Pless et al.

(10) Patent No.: US 8,478,419 B2
(45) Date of Patent: Jul. 2, 2013

(54) MODULATION AND ANALYSIS OF CEREBRAL PERFUSION IN EPILEPSY AND OTHER NEUROLOGICAL DISORDERS

(75) Inventors: Benjamin D. Pless, Atherton, CA (US); Brett Wingeier, San Francisco, CA (US)

(73) Assignee: NeuroPace, Inc., Mountain View, CA (US)

( * ) Notice: Subject to any disclaimer, the term of this patent is extended or adjusted under 35 U.S.C. 154(b) by 309 days.

(21) Appl. No.: 11/925,668

(22) Filed: Oct. 26, 2007

(65) Prior Publication Data
US 2008/0046026 A1 Feb. 21, 2008

Related U.S. Application Data

(62) Division of application No. 11/014,628, filed on Dec. 15, 2004, now Pat. No. 7,341,562.

(51) Int. Cl.
*A61N 1/365* (2006.01)
(52) U.S. Cl.
USPC .................................. 607/62; 607/3; 607/45
(58) Field of Classification Search
USPC .................................. 607/3, 45, 62
See application file for complete search history.

(56) References Cited

U.S. PATENT DOCUMENTS

| 4,817,627 | A | 4/1989 | Cohen et al. |
|---|---|---|---|
| 4,893,630 | A | 1/1990 | Bray |
| 6,006,124 | A | 12/1999 | Fischell et al. |
| 6,016,449 | A | 1/2000 | Fischell et al. |
| 6,018,682 | A | 1/2000 | Rise |
| 6,468,219 | B1 | 10/2002 | Njemanze |
| 6,629,990 | B2 | 10/2003 | Putz et al. |
| 6,792,302 | B2 | 9/2004 | Wintermark et al. |
| 6,810,285 | B2 | 10/2004 | Pless et al. |
| 2002/0161292 | A1 | 10/2002 | Wintermark et al. |
| 2003/0074032 | A1 | 4/2003 | Gliner |
| 2003/0176892 | A1* | 9/2003 | Shalev .............................. 607/3 |
| 2004/0039270 | A1 | 2/2004 | Keller et al. |
| 2004/0082978 | A1 | 4/2004 | Harrison et al. |
| 2005/0283200 | A1 | 12/2005 | Rezai et al. |

OTHER PUBLICATIONS

Gotman, J., "Automatic Seizure Detection: Improvements and Evaluation," Electroencephalog. Clin. Neurophysiol. (1990) 76(4): 317-24.
Wagner, H.R., et al., "Suppression of Cortical Epileptiform Activity by Generalized and Localized ECoG Desynchronization," Electroencephalogr. Clin. Neurophysiol. (1975): 39(5): 499-506.
Matsuura, T., et al., "Hennodynamics Evoked by Microelectrical Direct Stimulation in Rat Somatosensroy Cortex," Comp. Biochem. Physiol. A. Mo. I.. Integr. Physiol. (1999) Spet: 124(1): 47-52.
Bahar, S et al., "The Relationship Between Cerebral Blood Volume and Oxygenation Following Bipolar Stimulation of the Human Cortex: Evidence for an Initial Dip," American Epilepsy Society, Dec. 2004, New Orleans Poster Session.
Tarver, T. et al, "An Implantable Neurocybernetic Prosthesis System," http://www.ncbi.nlm.nih.gov, Jun. 12, 2007.

(Continued)

*Primary Examiner* — Christopher D Koharski
*Assistant Examiner* — Natasha Patel

(57) ABSTRACT

A system including an implantable neurostimulator device capable of modulating cerebral blood flow to treat epilepsy and other neurological disorders. In one embodiment, the system is capable of modulating cerebral blood flow (also referred to as cerebral perfusion) in response to measurements and other observed conditions. Perfusion may be increased or decreased by systems and methods according to the invention as clinically required.

19 Claims, 15 Drawing Sheets

OTHER PUBLICATIONS

ACTIVA Therapy Overview, http://www.medtronic.com/physician/activa/index.html, Jun. 5, 2007.

Tavalin, S.J., et al., "Mechanical Perturbation of Cultured Cortical Neurons Reveals a Stretch-Induced Delayed Depolarization," J. Neurophysiol. (1995).

U.S. Appl. No. 11/925,655 Office Action mailed Jun. 28, 2010.

Notice of Allowance mailed on Dec. 16, 2010 for U.S. Appl. No. 11/925,655.

Office Action (Non-Final Rejection) mailed Apr. 27, 2012 for U.S. Appl. No. 12/700,692.

* cited by examiner

MODULATION AND ANALYSIS OF CEREBRAL PERFUSION IN EPILEPSY AND OTHER NEUROLOGICAL DISORDERS

CROSS-REFERENCE TO RELATED APPLICATIONS

The present invention is a divisional of U.S. Ser. No. 11/014,628, filed Dec. 15, 2004, issued as U.S. Pat. No. 7,341,562, which is incorporated by reference herein.

BACKGROUND OF THE INVENTIONS

1. Field of the Inventions

The invention relates to medical devices for treating epilepsy, and more particularly to a system incorporating an implantable device capable of causing changes in cerebral blood flow.

2. Description of the Related Art

Epilepsy, a neurological disorder characterized by the occurrence of seizures (specifically episodic impairment or loss of consciousness, abnormal motor phenomena, psychic or sensory disturbances, or the perturbation of the autonomic nervous system), is debilitating to a great number of people. It is believed that as many as two to four million Americans may suffer from various forms of epilepsy. Research has found that its prevalence may be even greater worldwide, particularly in less economically developed nations, suggesting that the worldwide figure for epilepsy sufferers may be in excess of one hundred million.

Because epilepsy is characterized by seizures, its sufferers are frequently limited in the kinds of activities they may participate in. Epilepsy can prevent people from driving, working, or otherwise participating in much of what society has to offer. Some epilepsy sufferers have serious seizures so frequently that they are effectively incapacitated.

Furthermore, epilepsy is often progressive and can be associated with degenerative disorders and conditions. Over time, epileptic seizures often become more frequent and more serious, and in particularly severe cases, are likely to lead to deterioration of other brain functions (including cognitive function) as well as physical impairments.

The current state of the art in treating neurological disorders, particularly epilepsy, typically involves drug therapy and surgery. The first approach is usually drug therapy.

A number of drugs are approved and available for treating epilepsy, such as sodium valproate, phenobarbital primidone, ethosuximide, gabapentin, phenytoin, and carbamazepine, as well as a number of others. Unfortunately, those drugs typically have serious side effects, especially toxicity, and it is extremely important in most cases to maintain a precise therapeutic serum level to avoid breakthrough seizures (if the dosage is too low) or toxic effects (if the dosage is too high). The need for patient discipline is high, especially when a patient's drug regimen causes unpleasant side effects the patient may wish to avoid.

Moreover, while many patients respond well to drug therapy alone, a significant number (at least 20-30%) do not. For those patients, surgery is presently the best-established and most viable alternative course of treatment.

Currently practiced surgical approaches include radical surgical resection such as hemispherectomy, corticectomy, lobectomy and partial lobectomy, and less-radical lesionectomy, transection, and stereotactic ablation. Besides being less than fully successful, these surgical approaches generally have a high risk of complications, and can often result in damage to eloquent (i.e., functionally important) brain regions and the consequent long-term impairment of various cognitive and other neurological functions. Furthermore, for a variety of reasons, such surgical treatments are contraindicated in a substantial number of patients. And unfortunately, even after radical brain surgery, many epilepsy patients are still not seizure-free.

Electrical stimulation is an emerging therapy for treating epilepsy. However, currently approved and available electrical stimulation devices do not perform any detection of neural activity and apply electrical stimulation to neural tissue surrounding or near implanted electrodes somewhat indiscriminately; they are not responsive to relevant neurological conditions. Responsive stimulation, in which neurological activity is detected and electrical stimulation treatment is applied selectively, is in clinical trials at the time of this writing.

The NeuroCybernetic Prosthesis (NCP) from Cyberonics, for example, applies continuous electrical stimulation to the patient's vagus nerve. This approach has been found to reduce seizures by about 50% in about 50% of patients. Unfortunately, a much greater reduction in the incidence of seizures is needed to provide substantial clinical benefit.

The Activa device from Medtronic is a pectorally implanted continuous deep brain stimulator intended primarily to treat Parkinson's disease. In operation, it continuously supplies an intermittent electrical pulse stream to a selected deep brain structure where an electrode has been implanted. Continuous stimulation of deep brain structures for the treatment of epilepsy has not met with consistent success. To be effective in terminating seizures, it is believed that one effective site where stimulation should be performed is near the focus of the epileptogenic region. The focus is often in the neocortex, where continuous stimulation above a certain level may cause significant neurological deficit with clinical symptoms including loss of speech, sensory disorders, or involuntary motion. Accordingly, and to improve therapeutic efficacy over indiscriminate continuous stimulation, research has been directed toward automatic responsive epilepsy treatment based on a detection of imminent seizure.

A typical epilepsy patient experiences episodic attacks or seizures. Those events, neurological states, and epileptiform activity evident on the EEG shall be referred to herein as "ictal".

Most prior work on the detection and responsive treatment of seizures via electrical stimulation has focused on analysis of electroencephalogram (EEG) and electrocorticogram (ECoG) waveforms. In common usage, the term "EEG" is used to refer to signals representing aggregate neuronal activity potentials detectable via electrodes applied to a patient's scalp, though the term can also refer to signals obtained from deep in the patient's brain via depth electrodes and the like. Specifically, "ECoGs" refer to signals obtained from internal electrodes near the cortex of the brain (generally on or under the dura mater), but is often used to refer to direct brain signals from deeper structures as well; an ECoG is a particular type of EEG. Unless the context clearly and expressly indicates otherwise, the term "EEG" shall be used generically herein to refer to both EEG and ECoG signals, regardless of where in the patient's brain the electrodes are located.

It is generally preferable to be able to detect and treat a seizure at or near its beginning, or even before it begins. The beginning of a seizure is referred to herein as an "onset." However, it is important to note that there are two general varieties of seizure onsets. A "clinical onset" represents the beginning of a seizure as manifested through observable clinical symptoms, such as involuntary muscle movements or neurophysiological effects such as lack of responsiveness. An "electrographic onset" refers to the beginning, of detectable electrographic activity indicative of a seizure. An electrographic onset will frequently occur before the corresponding clinical onset, enabling intervention before the patient suffers symptoms, but that is not always the case. In addition, there are changes in the EEG that occur seconds or even minutes before the electrographic onset that can be identified, and may be used to facilitate intervention before clear electrographic or clinical onsets occur. This capability would be considered seizure anticipation, in contrast to the detection of a seizure or its onset. Seizure anticipation is much like weather prediction—there is an indication the likelihood has increased that a seizure will occur, but when exactly it will occur, or even if it will occur is not certain.

U.S. Pat. No. 6,018,682 to Rise describes an implantable seizure warning system that implements a form of the Gotman system. See, e.g., J. Gotman, Automatic seizure detection: improvements and evaluation, Electroencephalogr. Clin. Neurophysiol. 1990; 76(4): 317-24. However, the system described therein uses only a single detection modality, namely a count of sharp spike and wave patterns within a time period, and is intended to provide a warning of impending seizure activity in spite of a lack of evidence that spike and wave activity is sufficiently anticipatory of seizures. This is accomplished with relatively complex processing, including averaging over time and quantifying sharpness by way of a second derivative of the signal. The Rise patent does not disclose how the signals are processed at a low level, nor does it explain detection criteria in any specific level of detail.

U.S. Pat. No. 6,016,449 to Fischell, et al. (which is hereby incorporated by reference as though set forth in full herein), describes an implantable seizure detection and treatment system. In the Fischell system, various detection methods are possible, all of which essentially rely upon the analysis (either in the time domain or the frequency domain) of processed EEG signals. Fischell's controller is preferably implanted intracranially, but other approaches are also possible, including the use of an external controller. The processing, and detection techniques applied in Fischell are generally well suited for implantable use. When a seizure is detected, the Fischell system applies responsive electrical stimulation to terminate the seizure, a capability that will be discussed in further detail below.

All of these approaches provide useful information, and in some cases may provide sufficient information for accurate detection and or anticipation of most imminent epileptic seizures.

It has been found that many clinical neurological disorders are associated with abnormal blood flow patterns in the brain. These include epilepsy, movement disorders, and psychiatric disorders. It would therefore be advantageous to employ a system or method to monitor such abnormal blood flow patterns, either in isolation or in connection with abnormal electrographic activity, to identify the status of the disease state and to monitor the short-term and/or long-term progression of the disease state with the intention of correcting the abnormal blood flow patterns to provide clinical benefit. Such monitoring is preferably accomplished within the therapy delivery device (often a neurostimulator) to automatically adjust therapy delivery to the patient to more optimally bring about beneficial changes in brain blood flow patterns either acutely or more long term. Therapy delivery may be direct brain electrical stimulation, spinal cord stimulation, brain stem or peripheral nerve stimulation, or may be magnetic stimulation, somatosensory stimulation, or drug delivery. However, monitoring may include means not included in the therapy delivery device, with therapy being adjusted by a clinician. Monitoring of the brain blood flow can be accomplished by the periodic application of non-invasive imaging techniques including SPECT, PET, SISCOM, infrared, ultrasound, or impedance techniques.

As is well known, it has been suggested that it is possible to treat and terminate seizures by applying electrical stimulation to the brain. See, e.g., U.S. Pat. No. 6,016,449 to Fischell et al., and H. R. Wagner, et al., Suppression of cortical epileptiform activity by generalized and localized ECoG desynchronization, Electroencephalogr. Clin. Neurophysiol. 1975; 39(5): 499-506. It has further been found that electrical stimulation can modulate blood flow in the brain. Cortical stimulation increases blood flow within hundreds of milliseconds at the site of stimulation (T. Matsuura et al., "Hemodynamics evoked by microelectrical direct stimulation in rat somatosensory cortex." Comp. Biochem. Physiol. A. Mol. Integr. Physiol. September, 1999, 124(1): 47-52; see also S. Bahar et al., "THE RELATIONSHIP BETWEEN CEREBRAL BLOOD VOLUME AND OXYGENATION FOLLOWING BIPOLAR STIMULATION OF THE HUMAN CORTEX: EVIDENCE FOR AN INITIAL DIP," AES 12-2004 New Orleans Poster Session). Stimulation of other brain structures or through the use of transcranial magnetic stimulation can produce patterns of blood flow changes including increases or reductions of blood flow) in targeted areas.

At the current time, there is no known implantable device that is capable of treating abnormal neurological conditions, including seizures, by changing cerebral perfusion either acutely or chronically. Furthermore, there is no known implantable device that is capable of detecting and or anticipating seizures or other neurological events based on cerebral perfusion conditions and changes therein, alone or in combination with other observed conditions. As anticipated herein, modulation of blood perfusion in the brain may be employed for acute or chronic treatment of neurological conditions.

SUMMARY OF THE INVENTION

A system according to the invention includes an apparatus, preferably implantable, capable of modulating cerebral blood flow and/or sensing changes in cerebral blood flow, either globally or locally, and responding thereto to achieve acute and/or chronic changes in cerebral blood flow.

The invention provides for the use of electrical stimulation and other modalities of stimulation (including transcranial magnetic stimulation) directed at a variety of anatomical targets to produce changes in cortical blood flow to treat neurological disorders, including but not limited to epilepsy. Stimulation may be applied "open loop" (on a scheduled basis), or "closed loop" as a result of information from sensors, particularly blood flow, electrographic, or movement sensors. Therapy may also be provided on command by a physician, the patient, or a caregiver. Systems according to the invention may be adapted for implantable use, or may be partially or completely external to the patient.

Electrical stimulation may be applied directly to the cortex, or alternatively to deeper brain structures, or to the brain stem, spinal cord or to cranial or peripheral nerves. Electrical stimulation, when it is applied, may be pulsatile in nature or of an arbitrary waveform including sine-waves. Different stimulation patterns, and the location of the stimulation may be varied depending upon the brain state. For example, a hypoperfused seizure onset focus in the interictal state may receive a stimulation pattern specifically designed to maximize blood flow. As the brain transitions into a pre-seizure state as determined by characteristic changes in blood flow, electrographic evidence, or even by the patient feeling symptoms and communicating the information to the therapy device, the stimulation pattern may be beneficially changed to enhance blood flow in neural pathways (for instance in those pathways emanating from the seizure focus), or to decrease excitability at the seizure focus for example by stimulation of the caudate.

One system according to the invention includes an implanted control module, controllable via external equipment, that is capable of applying therapeutic intervention to alter cerebral blood flow via electrical, thermal, chemical, electromagnetic, or other therapy modalities set forth herein and described in greater detail below. Preferably, such stimulation is not provided continuously, but intermittently, and means are provided to verify the need and/or effects of blood flow stimulation according to the invention. For example, an external programmer may be used to command the implanted device to deliver stimulation, after which measurements are taken (via imaging techniques or other methods described herein, including automatic measurements taken by the implanted device) to verify the effects or progress of the therapy. Depending on the effects observed, the implanted device is programmed by the external programmer with a preferred therapy regimen.

In an embodiment of the invention, automatic measurements are taken by the implanted device via impedance plethysmography techniques. These measurements are recorded and later transferred to the external programmer via wireless telemetry, and may be used by a clinician to tailor therapy to the specific patient being treated.

A specific embodiment of a system according to the invention performs regular perfusion measurements and applies therapy automatically in response thereto. This embodiment includes an implanted control module, implanted electrodes on a seizure focus and on the caudate nucleus, and an implanted pulse oximetry perfusion sensor in the vicinity of the seizure focus. In addition, a perfusion sensor (with electrodes) may be implanted on the contralateral lobe from the seizure focus. After implant, baseline perfusion and electrographic data may be collected for at least several days and for several seizures while the patient recovers from surgery. Commanded stimulation studies may be performed to assess the effect of different stimulation parameters at the seizure focus and at the caudate on perfusion behavior. Stimulation at the seizure focus will generally increase perfusion (the seizure focus is generally hypo-perfused in the interictal period) whereas stimulation of brain stem structures or the caudate may decrease perfusion.

The implanted control module monitors perfusion at the epileptogenic focus, taking pulsed measurements every 30 seconds to save power. If sudden changes in perfusion are detected, the sampling rate may be increased for improved resolution. The control module runs a therapy algorithm to slowly increase the perfusion level at the epileptogenic focus to a target range by applying stimulation as programmed within a preset range of allowed parameters (pulse amplitude, pulse width, number of pulses in a burst, pulse to pulse interval, interval between bursts, rate of change allowed from burst to burst). If the perfusion level at the site of the seizure focus increases above the target range, the algorithm calls for the control module to stimulate other brain structures such as the caudate in an attempt to bring the perfusion level down to a target range (this target range may be different than the target used when stimulating the focus directly). The patient or a caregiver may be alerted if a trend towards increased perfusion of the epileptogenic focus occurs despite caudate stimulation. This would allow the use of an increased dose of antiseizure medication only when a breakthrough seizure is likely to occur.

It should be noted that epilepsy, and other neurological disorders treatable by a system according to the invention, vary greatly in symptomology and treatment strategies from patient to patient. For example, to give one example, although perfusion has generally been observed to be pathologically low and increase prior to an epileptic seizure, the reverse may be true in some patients or in some anatomical locations. Accordingly, the present invention as described in detail herein provides a framework for the diagnosis and treatment of neurological dysfunctions by sensing and responding to changes in cerebral blood flow, but specific treatment strategies should be determined, customized, and altered as clinical observations and experience dictate.

BRIEF DESCRIPTION OF THE DRAWINGS

These and other objects, features, and advantages of the invention will become apparent from the detailed description below and the accompanying drawings, in which.

DETAILED DESCRIPTION OF THE INVENTION

The invention is described below, with reference to detailed illustrative embodiments. It will be apparent that a system according to the invention may be embodied in a wide variety of forms. Consequently, the specific structural and functional details disclosed herein are representative and do not limit the scope of the invention.

Figure 1:
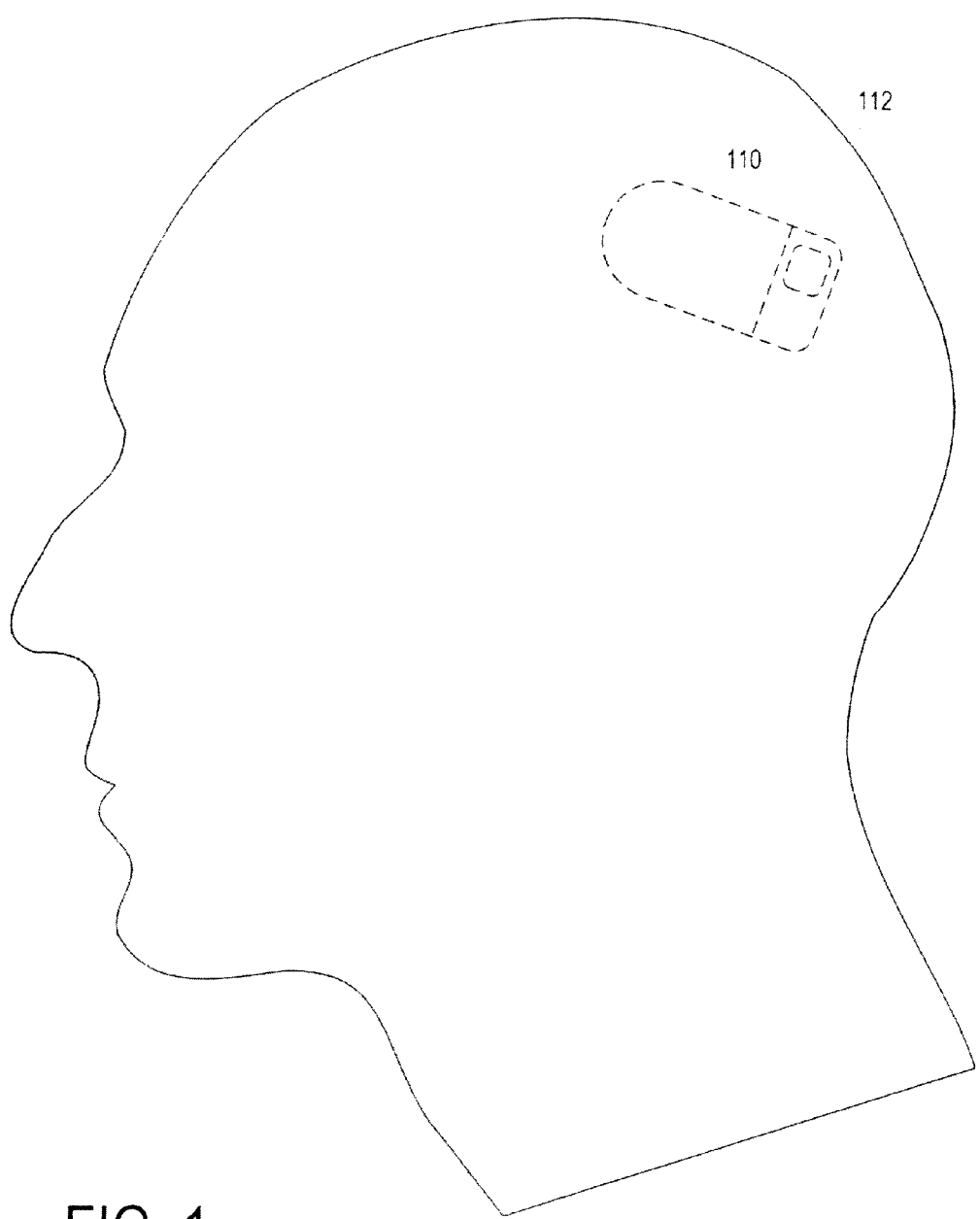
FIG. 1 is a schematic illustration of a patient's head showing the placement of an implantable neurostimulator according to an embodiment of the invention.

FIG. 1 depicts an intracranially implanted neurostimulator device 110 according to the invention, which in one embodiment is a small self-contained responsive neurostimulator located under the patient's scalp 112. As the term is used herein, a responsive neurostimulator is a device capable of detecting or anticipating ictal activity (or other neurological events) and providing electrical stimulation to neural tissue in response to that activity, where the electrical stimulation is specifically intended to terminate the ictal activity, treat a neurological event, prevent an unwanted neurological event from occurring, or lessen the severity or frequency of certain symptoms of a neurological disorder. As disclosed herein, the responsive neurostimulator detects ictal activity by systems and methods according to the invention.

Preferably, an implantable device according to the invention is capable of detecting or anticipating any kind of neurological event that has a representative electrographic signature. While the disclosed embodiment is described primarily as responsive to epileptic seizures, it should be recognized that it is also possible to respond to other types of neurological disorders, such as movement disorders (e.g. the tremors characterizing Parkinson's disease), migraine headaches, chronic pain, and neuropsychiatric disorders such as schizophrenia, obsessive-compulsive disorders, and depression. Preferably, neurological events representing any or all of these afflictions can be detected when they are actually occurring in an onset stage, or as a anticipatory precursor before clinical symptoms begin.

Figure 2:
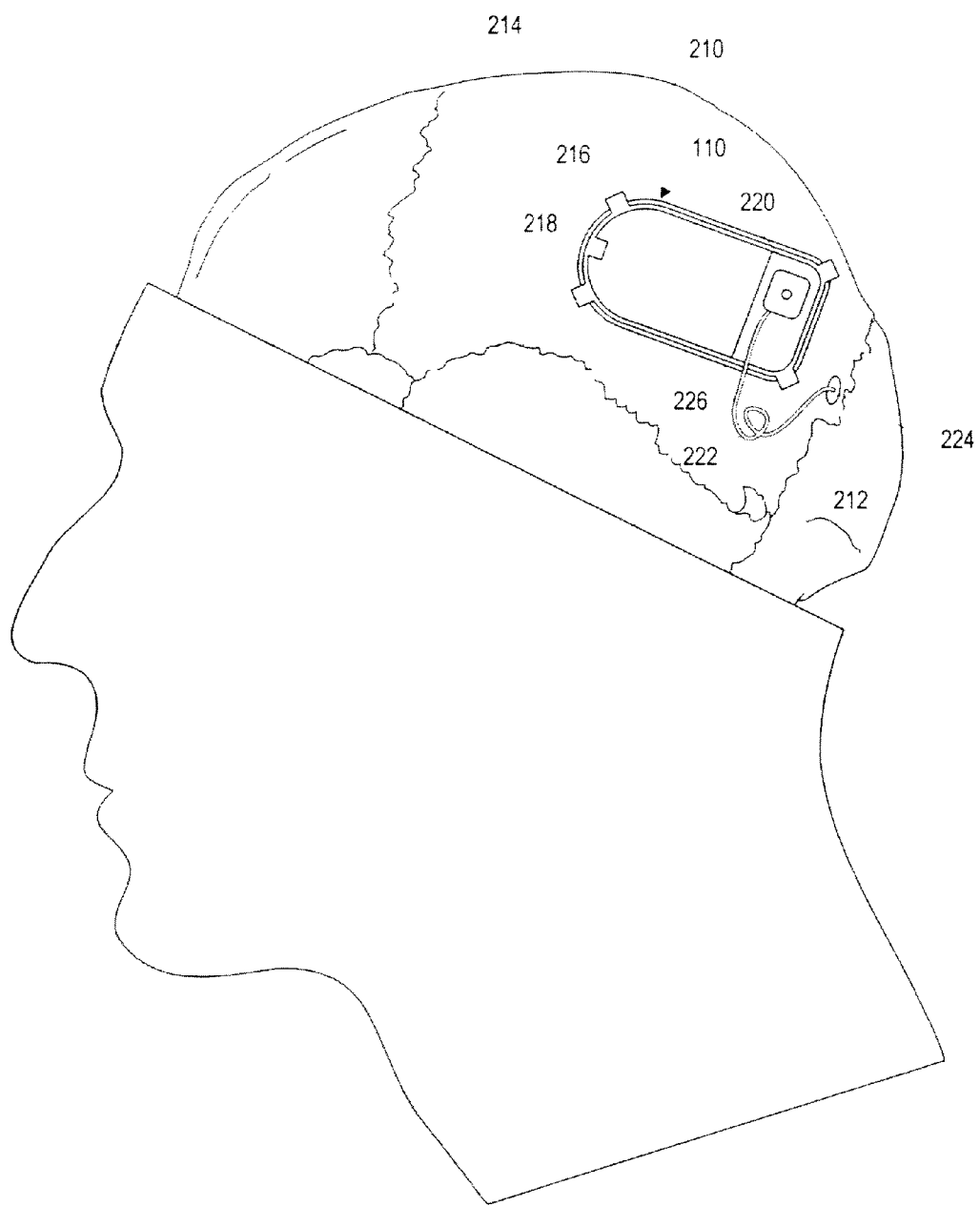
FIG. 2 is a schematic illustration of a patient's cranium showing the implantable neurostimulator of FIG. 1 as implanted, including leads extending to the patient's brain.

In the disclosed embodiment, the neurostimulator is implanted intracranially in a patient's parietal bone 210, in a location anterior to the lambdoid suture 212 (see FIG. 2). It should be noted, however, that the placement described and illustrated herein is merely exemplary, and other locations and configurations are also possible, in the cranium or elsewhere, depending on the size and shape of the device and individual patient needs, among other factors. The device 110 is preferably configured to fit the contours of the patient's cranium 214. In an alternative embodiment, the device 110 is implanted under the patients scalp 112 but external to the cranium; it is expected, however, that this configuration would generally cause an undesirable protrusion in the patient's scalp where the device is located. In yet another alternative embodiment, when it is not possible to implant the device intracranially, it may be implanted pectorally (not shown), with leads extending through the patient's neck and between the patient's cranium and scalp, as necessary.

It should be recognized that the embodiment of the device 110 described and illustrated herein is preferably a responsive neurostimulator for detecting and treating epilepsy by detecting seizures or their onsets or precursors, preventing and/or terminating such epileptic seizures, and responding to clusters of therapies as described herein.

In an alternative embodiment of the invention, the device 110 is not a responsive neurostimulator, but is an apparatus capable of detecting neurological conditions and events and performing actions in response thereto. The actions performed by such an embodiment of the device 110 need not be therapeutic, but may involve data recording or transmission, providing warnings to the patient, or any of a number of known alternative actions. Such a device will typically act as a diagnostic device when interfaced with external equipment, as will be discussed in further detail below.

The device 110 is implanted intracranially, is illustrated in greater detail in FIG. 2. The device 110 is affixed in the patient's cranium 214 by way of a ferrule 216. The ferrule 216 is a structural member adapted to fit into a cranial opening, attach to the cranium 214, and retain the device 110.

To implant the device 110, a craniotomy is performed in the parietal bone 210 anterior to the lambdoidal suture 212 to define an opening 218 slightly larger than the device 110. The ferrule 216 is inserted into the opening 218 and affixed to the cranium 214, ensuring a tight and secure fit. The device 110 is then inserted into and affixed to the ferrule 216.

As shown in FIG. 2, the device 110 includes a lead connector 220 adapted to receive one or more electrical leads, such as a first lead 222. The lead connector 220 acts to physically secure the lead 222 to the device 110, and facilitates electrical connection between a conductor in the lead 222 coupling an electrode to circuitry within the device 110. The lead connector 220 accomplishes this in a substantially fluid-tight environment with biocompatible materials.

The lead 222, as illustrated, and other leads for use in a system or method according to the invention, is a flexible elongated member having one or more conductors. As shown, the lead 222 is coupled to the device via the lead connector 220, and is generally situated on the outer surface of the cranium 214 (and under the patient's scalp 112), extending between the device 110 and a burr hole 224 or other cranial opening, where the lead 222 enters the cranium 214 and is coupled to a depth electrode (e.g., one of the outputs 412-418 of FIG. 4, in an embodiment in which the outputs are implemented as depth electrodes) implanted in a desired location in the patient's brain. If the length of the lead 222 is substantially greater than the distance between the device 110 and the burr hole 224, any excess may be urged into a coil configuration under the scalp 112. As described in U.S. Pat. No. 6,006,124 to Fischell et al., which is hereby incorporated by reference as though set forth fully herein, the burr hole 224 is sealed after implantation to prevent further movement of the lead 222; in an embodiment of the invention, a burr hole cover apparatus is affixed to the cranium 214 at least partially within the burr hole 224 to provide this functionality.

The device 110 includes a durable outer housing 226 fabricated from a biocompatible material. Titanium, which is light, extremely strong, and biocompatible, is used in analogous devices, such as cardiac pacemakers, and would serve advantageously in this context. As the device 110 is self-contained, the housing 226 encloses a battery and any electronic circuitry necessary or desirable to provide the functionality described herein, as well as any other features. As will be described in further detail below, a telemetry coil may be provided outside of the housing 226 (and potentially integrated with the lead connector 220) to facilitate communications between the device 110 and external devices. Other portions of a system according to the invention may also be positioned outside of the housing 226, as will be described in further detail below.

The neurostimulator configuration described herein and illustrated in FIG. 2 provides several advantages over alternative designs. First, the self-contained nature of the neurostimulator substantially decreases the need for access to the device 110, allowing the patient to participate in normal life activities. Its small size and intracranial placement causes a minimum of cosmetic disfigurement. The device 110 will fit in an opening in the patient's cranium, under the patient's scalp, with little noticeable protrusion or bulge. The ferrule 216 used for implantation allows the craniotomy to be performed and fit verified without the possibility of breaking the device 110, and also provides protection against the device 110 being pushed into the brain under external pressure or impact. A further advantage is that the ferrule 216 receives any cranial bone growth, so at explant, the device 110 can be replaced without removing any bone screws—only the fasteners retaining the device 110 in the ferrule 216 need be manipulated.

Figure 3:
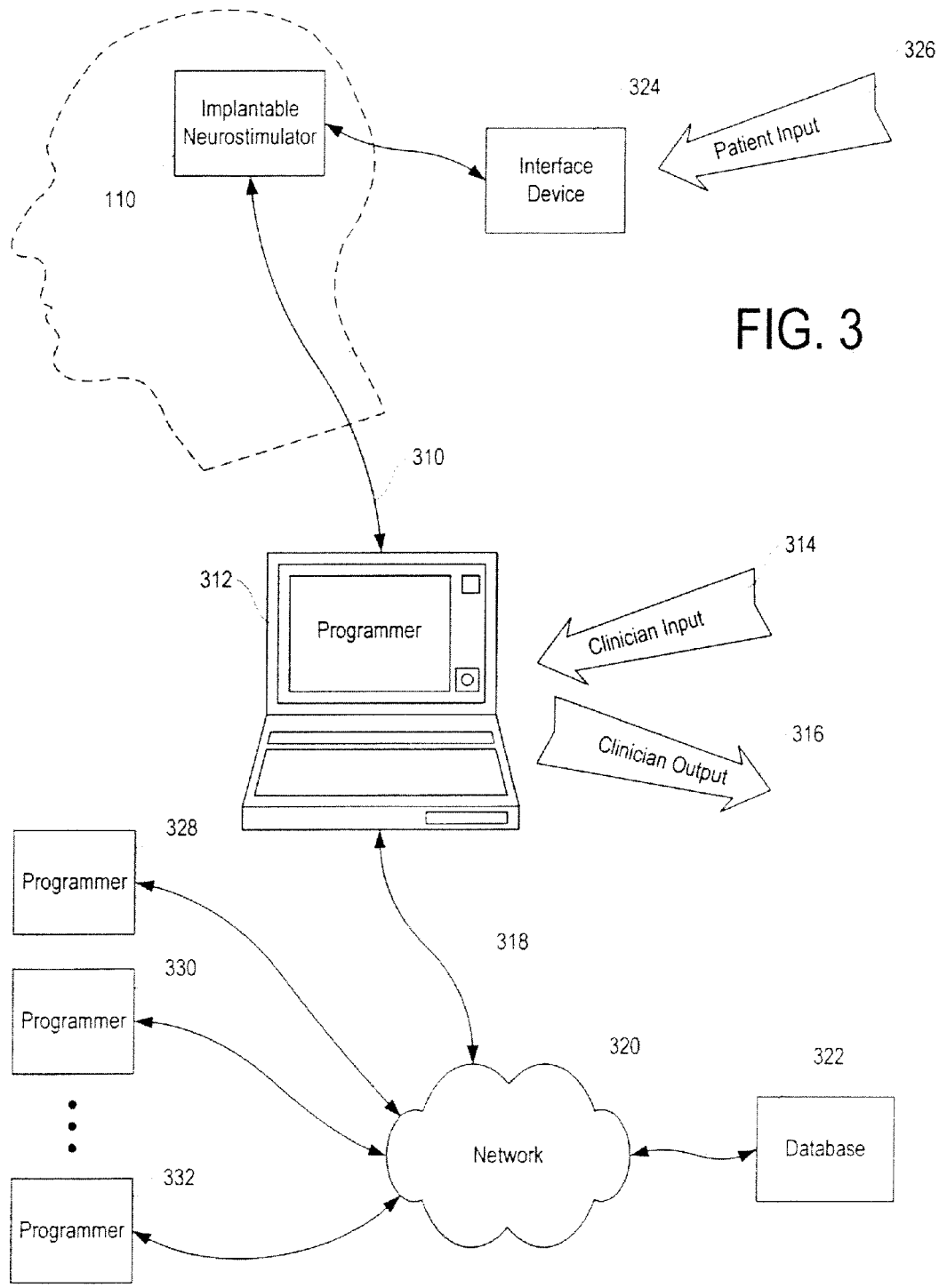
FIG. 3 is a block diagram illustrating a system context in which an implantable neurostimulator according to the invention is implanted and operated.

As stated above, and as illustrated in FIG. 3, a neurostimulator according to the invention operates in conjunction with external equipment. The implantable neurostimulator device 110 is mostly autonomous (particularly when performing its usual sensing, detection, and stimulation capabilities), but preferably includes a selectable part-time wireless link 310 to external equipment such as a programmer 312. In the disclosed embodiment of the invention, the wireless link 310 is established by moving a wand (or other apparatus) having communication capabilities and coupled to the programmer 312 into communication range of the implantable neurostimulator device 110. The programmer 312 can then be used to manually control the operation of the device, as well as to transmit information to or receive information from the implantable neurostimulator 110. Several specific capabilities and operations performed by the programmer 312 in conjunction with the device will be described in further detail below.

The programmer 312 is capable of performing a number of advantageous operations in connection with the invention. In particular, the programmer 312 is able to specify and set variable parameters in the implantable neurostimulator device 110 to adapt the function of the device to meet the patient's needs, upload or receive data (including but not limited to stored EEG waveforms parameters, or logs of actions taken) from the implantable neurostimulator device 110 to the programmer 312, download or transmit program code and other information from the programmer 312 to the implantable neurostimulator 310, or command the implantable neurostimulator 110 to perform specific actions or change modes as desired by a physician operating the programmer 312. To facilitate these functions, the programmer 312 is adapted to receive clinician input 314 and provide clinician output 316; data is transmitted between the programmer 312 and the implantable neurostimulator device 110 over the wireless link 310.

The programmer 312 may be used at a location remote from the implantable neurostimulator 110 if the wireless link 310 is enabled to transmit data over long distances. For example, the wireless link 310 may be established by a short-distance first link between the implantable neurostimulator device 110 and a transceiver, with the transceiver enabled to relay communications over long distances to a remote programmer 312, either wirelessly (for example, over a wireless computer network) or via a wired communications link (such as a telephonic circuit or a computer network).

The programmer 312 may also be coupled via a communication link 318 to a network 320 such as the Internet. This allows any information uploaded from the implantable neurostimulator device 110, as well as any program code or other information to be downloaded to the implantable neurostimulator device 110, to be stored in a database 322 at one or more data repository locations (which may include various servers and network-connected programmers like the programmer 312). This would allow a patient (and the patient's physician) to have access to important data, including past treatment information and software updates, essentially anywhere in the world where there is a programmer (like the programmer 312) and a network connection. Alternatively, the programmer 312 may be connected to the database 322 over a trans-telephonic link.

In yet another alternative embodiment of the invention, the wireless link 310 from the implantable neurostimulator 110 may enable a transfer of data from the neurostimulator 110 to the database 322 without any involvement by the programmer 312. In this embodiment, as with others, the wireless link 310 may be established by a short-distance first link between the implantable neurostimulator 110 and a transceiver, with the transceiver enabled to relay communications over long distances to the database 322, either wirelessly (for example, over a wireless computer network) or via a wired communications link (such as trans-telephonically over a telephonic circuit, or over a computer network).

In the disclosed embodiment, the implantable neurostimulator 110 is also adapted to receive communications from an interface device 324, typically controlled by the patient or a caregiver. Accordingly, patient input 326 from the interface device 324 is transmitted over a wireless link to the implantable neurostimulator device 110; such patient input 326 may be used to cause the implantable neurostimulator device 110 to switch modes (on to off and vice versa, for example) or perform an action (e.g., store a record of EEG data). Preferably, the interface device 324 is able to communicate with the implantable neurostimulator 110 through the communication subsystem 430 (FIG. 4), and possibly in the same manner the programmer 312 does. The link may be unidirectional (as with a magnet and GMR sensor as described below), allowing commands to be passed in a single direction from the interface device 324 to the implantable neurostimulator 110, but in an alternative embodiment of the invention is bidirectional, allowing status and data to be passed back to the interface device 324. Accordingly, the interface device 324 may be a programmable PDA or other hand-held computing device, such as a Palm Pilot® or PocketPC®. However, a simple form of interface device 324 may take the form of a permanent magnet, if the communication subsystem 430 is adapted to identify magnetic field and interruptions therein as communication signals.

In various embodiments of the invention, the interface device 324 may also include additional functions. In one embodiment, the interface device 324 may include an alert capability, enabling the neurostimulator device 110 to transmit an alert to the interface device 324 to provide a warning or other information to the patient. The interface device 324 may also include therapy functions, including but not limited to transcranial magnetic stimulation (TMS) capabilities. Such therapy functions may be controlled by the neurostimulator device 110, the interface device 324 itself, or some other device on the network.

The implantable neurostimulator device 100 (FIG. 1) generally interacts with the programmer 312 (FIG. 3) as described below. Data stored in the memory subsystem 526 (FIG. 5) can be retrieved by the patient's physician through the wireless communication link 310, which operates through the communication subsystem (communication subsystem 430 of FIG. 4, and communication subsystem 530 of FIG. 5) of the implantable neurostimulator 110. In connection with the invention, a software operating program run by the programmer 312 allows the physician to read out a history of neurological events detected including EEG information before, during and after each neurological event, as well as specific information relating to the detection of each neurological event. The programmer 312 also allows the physician to specify or alter any programmable parameters of the implantable neurostimulator 110. The software operating program also includes tools for the analysis and processing of recorded EEG records to assist the physician in developing optimized seizure detection parameters for each specific patient.

In an embodiment of the invention, the programmer 312 is primarily a commercially available PC, laptop computer, or workstation having a CPU, keyboard, mouse and display, and running a standard operating system such as Microsoft Windows®, Lunix®, Unix®, or Apple Mac OS®. It is also envisioned that a dedicated programmer apparatus with a custom software package (which may not use a standard operating system) could be developed.

When running the computer workstation software operating program, the programmer 312 can process, store, play back and display on the display the patient's EEG signals, as previously stored by the implantable neurostimulator 110 of the implantable neurostimulator device.

The computer workstation software operating program also has the capability to simulate the detection and anticipation of epileptiform activity. Furthermore, the software operating program of the present invention has the capability to allow a clinician to create or modify a patient-specific collection of information comprising, in one embodiment, algorithms, and algorithm parameters for epileptiform activity detection. The patient-specific collection of detection algorithms and parameters used for neurological activity detection according to the invention will be referred to herein as a detection template or patient-specific template, in conjunction with other information and parameters generally transferred from the programmer to the implanted device (such as stimulation parameters, time schedules, and other patient-specific information), make up a set of operational parameters for the neurostimulator. In the disclosed embodiment of the invention, the patient-specific template includes information about the parameters needed to identify clusters of events, as will be described in further detail below.

Following the development of a patient-specific template on the programmer 312, the patient-specific template would be downloaded through the communications link 310 from the programmer 312 to the implantable neurostimulator 110.

The patient-specific template is used by the detection subsystem 522 and the CPU 528 (FIG. 5) of the implantable neurostimulator 110 to detect epileptiform activity in the patient's EEG signals, which can be programmed by a clinician to result in responsive stimulation of the patient's brain, as well as the storage of EEG records before and after the detection, facilitating later clinician review.

Preferably, the database 322 is adapted to communicate over the network 320 with multiple programmers, including the programmer 312 and additional programmers 328, 330, and 332. It is contemplated that programmers will be located at various medical facilities and physicians' offices at widely distributed locations. Accordingly, if more than one programmer has been used to upload EEG records from a patient's implantable neurostimulator 110, the EEG records will be aggregated via the database 322 and available thereafter to any of the programmers connected to the network 320, including the programmer 312.

Figure 4:
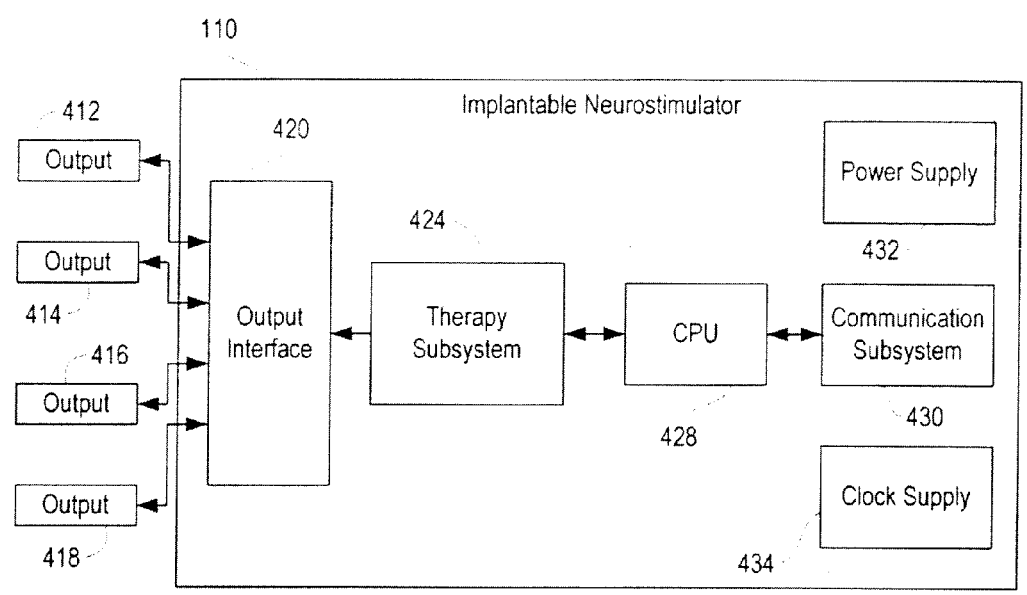
FIG. 4 is a block diagram illustrating the major functional subsystems of an implantable cerebral blood flow modulation device according to the invention.

FIG. 4 depicts a schematic block diagram of a neurostimulator system according to the invention, including an embodiment of the implantable neurostimulator device 110 comprising a small self-contained externally programmable and controlled neurostimulator that is intracranially implanted.

FIG. 4 is an overall block diagram of the implantable neurostimulator device 110 used to modulate cerebral blood flow according to the invention. Inside the housing of the neurostimulator device 110 are several subsystems making up the device. The implantable neurostimulator device 110 is capable of being coupled to a plurality of outputs 412, 414, 416, and 418 for various types of stimulation as described herein. In the illustrated embodiment, the coupling is accomplished through a lead connector.

The outputs 412-418, each of which may be configured to provide electrical, magnetic, chemical, thermal, or other types of stimulation, are in contact with the patient's brain or are otherwise advantageously located near locations of interest in the patient's brain, where perfusion is desired to be modulated, or from which other areas of the brain may be modulated. Each of the outputs 412-418 is electrically coupled to an output interface 420.

The therapy subsystem 424, which is coupled to the output interface 420, is capable of applying electrical and various other types of stimulation to neurological tissue through the outputs 412-418. This can be accomplished in any number of different manners. For example, with electrical stimulation, it may be advantageous in some circumstances to provide stimulation in the form of a substantially continuous stream of pulses, or on a scheduled basis. It is contemplated that the parameters of the stimulation signal (e.g., frequency, duration, waveform) provided by the therapy subsystem 424 would be specified by other subsystems in the implantable device 110, and may be received from external equipment such as the programmer 312, as will be described in further detail below.

In accordance with the invention, the therapy subsystem 424 may also provide for other types of stimulation, besides electrical stimulation described above. In particular, in certain circumstances, it may be advantageous to provide audio, visual, or tactile signals to the patient, to provide somatosensory electrical stimulation to locations other than the brain, or to deliver a drug or other therapeutic agent (either alone or in conjunction with stimulation).

Also in the implantable neurostimulator device 110 is a CPU 428, which can take the form of a microcontroller. The CPU 428 is capable of coordinating the actions of the device 110 and providing different therapies on different schedules (and at different locations) to the outputs 412-418 via the output interface 420, all according to programming and commands received from the programmer 312 and the patient interface device 324 (FIG. 3).

Also provided in the implantable neurostimulator device 110, and coupled to the CPU 428 is a communication subsystem 430. The communication subsystem 430 enables communication between the device 110 and the outside world, particularly the external programmer 312 and patient interface device 324, both of which are described above with reference to FIG. 3, and are used with the disclosed embodiment to command and program the device 110. As set forth above, the disclosed embodiment of the communication subsystem 430 includes a telemetry coil (which may be situated outside of the housing of the implantable neurostimulator device 110) enabling transmission and reception of signals, to or from an external apparatus, via inductive coupling. Alternative embodiments of the communication subsystem 430 could use an antenna for an RF link or an audio transducer for an audio link. Preferably, the communication subsystem 430 also includes a GMR (giant magnetoresistive effect) sensor to enable receiving simple signals (namely the placement and removal of a magnet) from a patient interface device; this capability can be used to initiate EEG recording as will be described in further detail below.

If the therapy subsystem 424 includes the audio capability set forth above, it may be advantageous for the communication subsystem 430 to cause the audio signal to be generated by the therapy subsystem 424 upon receipt of an appropriate indication from the patient interface device (e.g., the magnet used to communicate with the GMR sensor of the communication subsystem 430, thereby confirming to the patient or caregiver that a desired action will be performed, e.g. that an EEG record will be stored.

Rounding out the subsystems in the implantable neurostimulator device 110 are a power supply 432 and a clock supply 434. The power supply 432 supplies the voltages and currents necessary for each of the other subsystems. The clock supply 434 supplies substantially all of the other subsystems with any clock and timing signals necessary for their operation, including a real-time clock signal to coordinate programmed and scheduled actions.

As described above, the described embodiment is adapted to be used in an implanted environment to modulate a patient's cerebral blood flow for the control of epilepsy or other neurological disorders.

Figure 5:
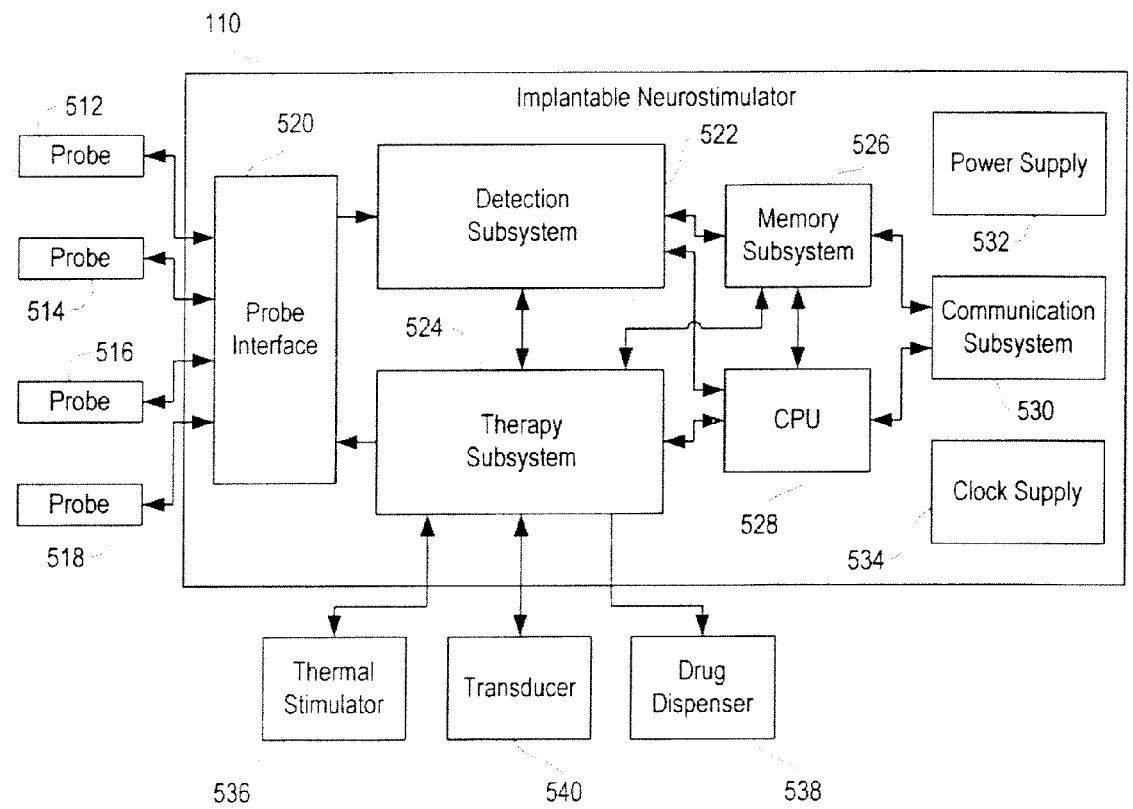
FIG. 5 is a block diagram illustrating the major functional subsystems of an implantable responsive blood flow modulation device according to the invention.

FIG. 5 depicts a schematic block diagram of an implantable responsive neurostimulator system according to the invention. The embodiment illustrated in FIG. 5 includes the capabilities of the programmable neurostimulator described with reference to FIG. 4, and is capable of acting responsively as set forth below. As the term is used herein, a responsive neurostimulator is a device capable of detecting undesired activity (or other neurological events) and providing electrical stimulation to neural tissue in response to that activity, where the electrical stimulation is specifically intended to terminate the undesired activity, treat a neurological event, prevent an unwanted neurological event from occurring, or lessen the severity or frequency of certain symptoms of a neurological disorder.

It should be recognized that the embodiment of the device described and illustrated herein is preferably a responsive neurostimulator for detecting and treating epilepsy by detecting seizure precursors and preventing and/or terminating epileptic seizures. It will be recognized, and it is described elsewhere herein, that similar methods and devices may be used to treat other neurological disorders as well.

FIG. 5 is an overall block diagram of the implantable neurostimulator device 110 used to measurement, detection, and treatment according to the invention. Inside the housing of the neurostimulator device 110 are several subsystems making up the device. The implantable neurostimulator device 110 is capable of being coupled to a plurality of probes 512, 514, 516, and 518 (each of which may be individually or together connected to the implantable neurostimulator device 110 via one or more leads) for sensing and stimulation. In the illustrated embodiment, the coupling is accomplished through a lead connector. Although four probes are shovel in FIG. 5, it should be recognized that any number is possible, and in the embodiment described in detail herein, eight electrodes on two leads are used. In fact, it is possible to employ an embodiment of the invention that uses a single lead with at least two electrodes, or two leads each with at least a single electrode (or with a second electrode provided by a conductive exterior portion of the housing in one embodiment), although bipolar sensing between two closely spaced electrodes on a lead is preferred to minimize common mode signals including noise.

The probes (as disclosed, electrodes) 512-518 are in contact with the patient's brain or are otherwise advantageously located to receive signals or provide electrical stimulation. Each of the electrodes 512-518 is also electrically coupled to a probe interface 520. Preferably, the probe interface is capable of selecting each electrode (or other sensor or probe) as required for sensing and stimulation; accordingly the probe interface is coupled to a detection subsystem 522 and a stimulation subsystem 524 (which, in an embodiment of the invention, may provide therapy and have outputs other than electrical stimulation, as described below). The electrode interface may also provide any other features, capabilities, or aspects, including but not limited to amplification, isolation, and charge-balancing functions, that are required for a proper interface with neurological tissue and not provided by any other subsystem of the device 110.

The detection subsystem 522 includes and serves primarily as a cerebral blood flow and EEG waveform analyzer; detection is accomplished in conjunction with a central processing unit (CPU) 528. The analysis functions are adapted to receive signals from the probes 512-518, through the probe interface 520, and to process those signals to identify neurological activity indicative of a seizure or a precursor to a seizure. One way to implement EEG analysis functionality is disclosed in detail in U.S. Pat. No. 6,016,449 to Fischell et al., incorporated by reference above. Additional inventive methods are described in U.S. Pat. No. 6,810,285 to Pless et al., entitled "SEIZURE SENSING AND DETECTION USING AN IMPLANTABLE DEVICE," of which details will be set forth below (and which is also hereby incorporated by reference as though set forth in full). The detection subsystem may optionally also contain further sensing and detection capabilities, including but not limited to parameters derived from other physiological conditions (such as electrophysiological parameters, temperature, blood pressure, etc.). In general, prior to analysis, the detection subsystem performs amplification, analog to digital conversion, and multiplexing functions on the signals in the sensing channels received from the probes 512-518.

The therapy subsystem 524 is capable of applying electrical and other types of stimulation to neurological tissue through the probes 512-518, to the extent such probes are capable of applying stimulation. This can be accomplished in any number of different manners. For example, it may be advantageous in some circumstances to provide electrical or other stimulation in the form of a substantially continuous stream of pulses, or on a scheduled basis. Preferably, therapeutic stimulation is provided in response to abnormal neurological events detected by the EEG analyzer function of the detection subsystem 522 and to modulate cerebral blood flow as described herein. As illustrated in FIG. 5, the therapy subsystem 524 and the analysis functions of the detection subsystem 522 are in communication; this facilitates the ability of the therapy subsystem 524 to provide responsive stimulation as well as an ability of the detection subsystem 522 to blank the amplifiers while electrical stimulation is being performed to minimize stimulation artifacts. It is contemplated that the parameters of the stimulation signal (e.g., frequency, duration, waveform) provided by the therapy subsystem 524 would be specified by other subsystems in the implantable device 110, as will be described in further detail below.

In accordance with the invention, the therapy subsystem 524 may also provide for other types of stimulation, besides electrical stimulation described above. Such stimulation may be provided through the probes 512-518, or alternative therapy outputs may be provided, such as a thermal stimulator 536, a drug dispenser 538, or a transducer 540, which may be adapted for placement in, on, or near the brain, or elsewhere. In particular, in certain circumstances, it may be advantageous to provide audio, visual, or tactile signals to the patient, to provide somatosensory electrical stimulation to locations other than the brain, or to deliver a drug or other therapeutic agent (either alone or in conjunction with stimulation).

Also in the implantable neurostimulator device 110 is a memory subsystem 526 axed the CPU 528, which can take the form of a microcontroller. The memory subsystem is coupled to the detection subsystem 522 (e.g., for receiving and storing data representative of sensed EEG signals and evoked responses), the therapy subsystem 524 (e.g., for providing stimulation waveform parameters to the therapy subsystem), and the CPU 528, which can control the operation of (and store and retrieve data from) the memory subsystem 526. In addition to the memory subsystem 526, the CPU 528 is also connected to the detection subsystem 522 and the therapy subsystem 524 for direct control of those subsystems.

Also provided in the implantable neurostimulator device 110, and coupled to the memory subsystem 526 and the CPU 528, is a communication subsystem 530. The communication subsystem 530 enables communication between the device 110 and the outside world, particularly the external programmer 312 and patient interface device 324, both of which are described above with reference to FIG. 3. As set forth above (with reference to FIG. 4 and the communication subsystem 430), the disclosed embodiment of the communication subsystem 530 includes a telemetry coil (which may be situated outside of the housing of the implantable neurostimulator device 110) enabling transmission and reception of signals, to or from an external apparatus, via inductive coupling. Alternative embodiments of the communication subsystem 530 could use an antenna for an RF link or an audio transducer for an audio link. Preferably, the communication subsystem 530 also includes a GMR (giant magnetoresistive effect) sensor to enable receiving simple signals (namely the placement and removal of a magnet) from a patient interface device; this capability can be used to initiate EEG recording as will be described in further detail below.

If the therapy subsystem 524 includes the audio capability set forth above (e.g., via the transducer 540), it may be advantageous for the communication subsystem 530 to cause the audio signal to be generated by the therapy subsystem 524 upon receipt of an appropriate indication from the patient interface device (e.g., the magnet used to communicate with the GMR sensor of the communication subsystem 530), thereby confirming to the patient or caregiver that a desired action will be performed, e.g. that an EEG record will be stored.

Rounding out the subsystems in the implantable neurostimulator device 110 are a power supply 532 and a clock supply 534. The power supply 532 supplies the voltages and currents necessary for each of the other subsystems. The clock supply 534 supplies substantially all of the other subsystems with any clock and timing signals necessary for their operation, including a real-time clock signal to coordinate programmed and scheduled actions and the timer functionality used by the detection subsystem 522 that is described in detail below.

It should be observed that while the memory subsystem 526 is illustrated in FIG. 5 as a separate functional subsystem, the other subsystems may also require various amounts of memory to perform the functions described above and others. Furthermore, while the implantable neurostimulator device 110 is preferably a single physical unit (i.e., a control module) contained within a single implantable physical enclosure, namely the housing described above, other embodiments of the invention might be configured differently. The neurostimulator 110 may be provided as an external unit not adapted for implantation, or it may comprise a plurality of spatially separate units each performing a subset of the capabilities described above, some or all of which might be external devices not suitable for implantation. Also, it should be noted that the various functions and capabilities of the subsystems described above may be performed by electronic hardware, computer software (or firmware), or a combination thereof. The division of work between the CPU 528 and the other functional subsystems may also vary—the functional distinctions illustrated in FIG. 5 may not reflect the partitioning and integration of functions in a real-world system or method according to the invention.

Figure 6:
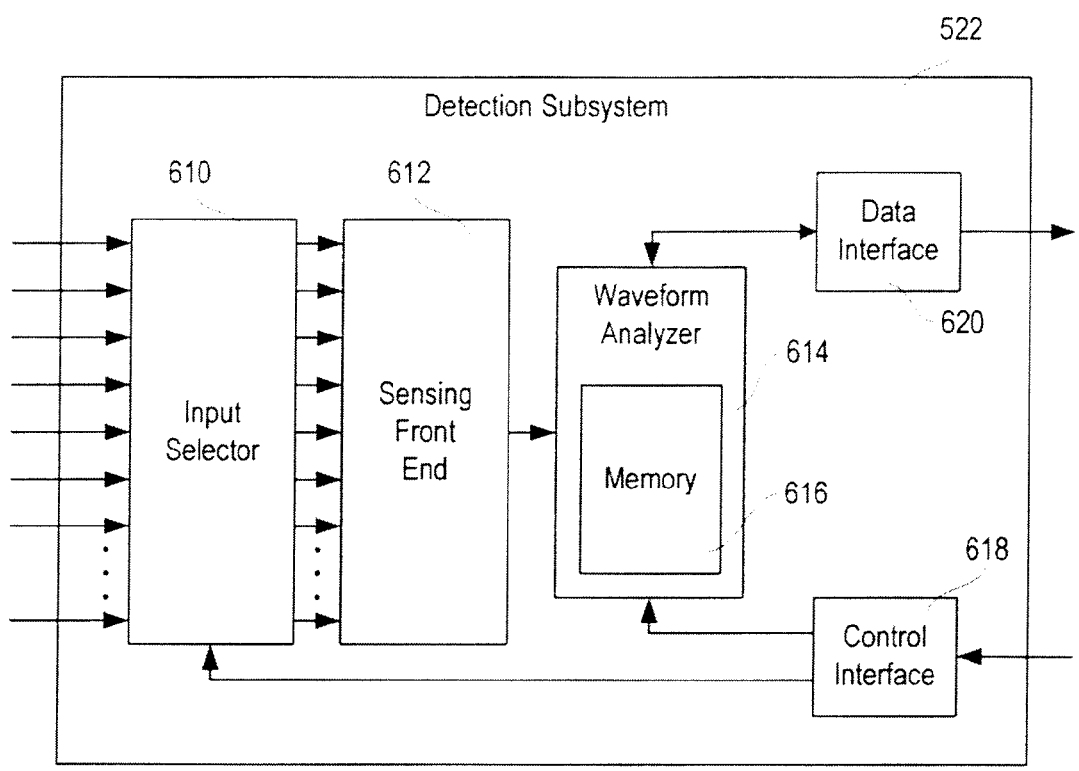
FIG. 6 is a block diagram illustrating the functional components of the detection subsystem of the implantable device shown in FIG. 4.

FIG. 6 illustrates details of the detection subsystem 522 (FIG. 5). Inputs from the probes 512-518 are on the left, and connections to other subsystems are on the right.

Signals received from the electrodes 512-518 (as routed through the probe interface 520) are received in an input selector 610. The input selector 610 allows the device to select which probes (of the probes 512-518) should be routed to which individual sensing channels of the detection subsystem 522, based on commands received through a control interface 618 from the memory subsystem 526 or the CPU 528 (FIG. 5). Preferably, for electrographic and impedance measurements, each sensing channel of the detection subsystem 522 receives a bipolar signal representative of the difference in electrical potential between two selectable electrodes. Accordingly, the electrode selector 610 provides signals corresponding to each pair of selected electrodes (of the probes 512-518) to a sensing front end 612, which performs amplification, analog to digital conversion, and multiplexing functions on the signals in the sensing channels.

A multiplexed input signal representative of all active sensing channels is then fed from the sensing front end 612 to a waveform analyzer 614. The waveform analyzer 614 is preferably a special-purpose digital signal processor (DSP) adapted for use with the invention, or in an alternative embodiment, may comprise a programmable general-purpose DSP. In the disclosed embodiment, the waveform analyzer has its own scratchpad memory area 616 used for local storage of data and program variables when the signal processing is being performed. In either case, the signal processor performs suitable measurement and detection methods described generally above and in greater detail below. Any results from such methods, as well as any digitized signals intended for storage transmission to external equipment, are passed to various other subsystems of the neurostimulator device 110, including the memory subsystem 526 and the CPU 528 (FIG. 5) through a data interface 620. Similarly, the control interface 618 allows the waveform analyzer 614 and the input selector 610 to be in communication with the CPU 528.

Figure 7:
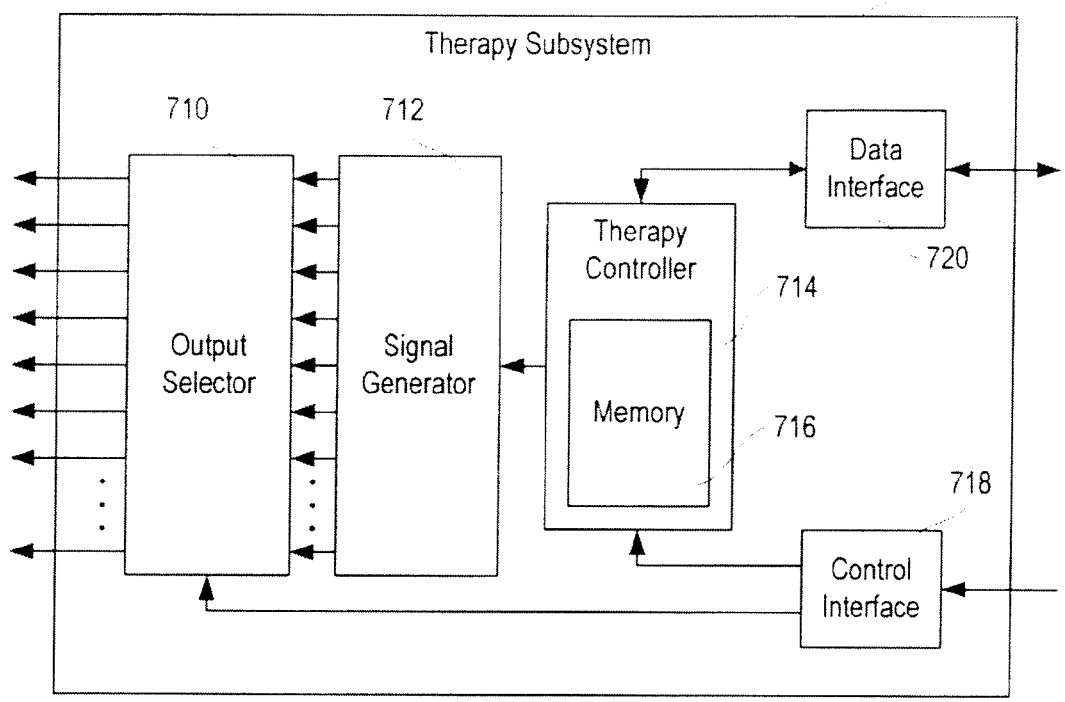
FIG. 7 is a block diagram illustrating the functional components of the therapy subsystem of the implantable device shown in FIG. 4.

FIG. 7 illustrates the components functionally present in an exemplary therapy subsystem 524 according to the invention. Through an output selector 710, the therapy subsystem 524 is capable of driving a number of outputs, including the thermal stimulator 536, the drug dispenser 538, and the audio transducer 540 illustrated in FIG. 5. Other outputs include leads for electrical stimulation and other stimulators as described in greater detail below with reference to FIGS. 8-11 and 13. Preferably, the output selector 710 is configured and may be programmed to drive more than one output, either in sequence or simultaneously.

The nature of the outputs is defined by a signal generator 712, advantageously designed to be able to produce different types of output signals for different types of outputs. For example, for electrical stimulation, biphasic pulsatile stimulation or low-frequency sine wave stimulation may be advantageous signals to generate, whereas for a burst of thermal stimulation, a single-polarity longer-duration pulse may be more appropriate. For various forms of active sensing described in detail below (in which a physiological or other physical response to an applied stimulus is measured), signals generated by the signal generator 712 are preferably coordinated with measurements made by the detection subsystem 522 (FIG. 5).

Such coordination and control of the signal generator 712 is accomplished through a therapy controller 714, which may include memory 716 to "play back" therapy waveforms and for other purposes—such waveforms may also be received via a data interface 720 from the main memory subsystem 526 or the CPU 528. The therapy controller receives input from a control interface 718, which is coupled to the CPU 528, thereby allowing the CPU 528 to control both the therapy subsystem 524 and the detection subsystem 522. Through the control interface 718, the CPU 528 is also capable of controlling the application of therapy (or other stimulation) to a desired combination of outputs via the output selector 710.

FIGS. 8-13 illustrate several embodiments of probes advantageously usable in a system according to the invention to measure and modulate perfusion. The chronically implantable probes illustrated in FIGS. 8-13 are advantageously connected to a device 110 according to the invention, and in the illustrated embodiments, have distal ends generally 0.5-3 mm in diameter, are at least partially flexible, and are of a length sufficient to reach from the device 110 to a desired target. The illustrations are schematic in nature and are not to scale. The probes of FIGS. 8-13 are illustrated as generally cylindrical depth probes, capable of being positioned within the gray or white matter of a patient's brain, but it should be recognized that surface cortical probes are also advantageous in certain embodiments; the differences between the illustrated probes and their cortical counterparts would be known to a practitioner of ordinary skill, and would primarily entail a different (paddle-shaped) physical configuration at the distal end.

Figure 8:
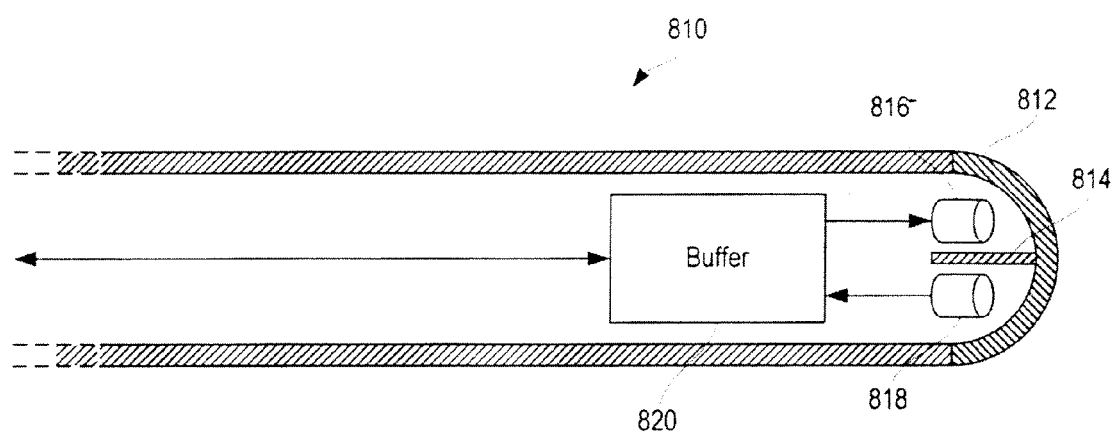
FIG. 8 is a schematic cutaway diagram of an optical sensing and stimulation probe according to the invention.

Referring now to FIG. 8, an optical probe 810 capable of measuring cerebral perfusion and applying optical stimulation is illustrated. The probe 810 includes an optically translucent distal tip 812 and opaque barrier 814 separating a light source 816 (typically one or more light emitting diodes, or LEDs) and a light sensor 818 (typically a photodiode, but it may also include a CCD or other light sensor). In the illustrated embodiment, the light source 816 and light sensor 818 are connected to a buffer 820, which in turn is coupled to the device 110. This configuration allows a single set of control wires (typically a pair) to both send information bi-directionally between the probe 810 and the device 110. In an alternative embodiment, the buffer 820 may be omitted and multiple control links may be established between the device 110 and the light source 816 and sensor 818; in this embodiment the probe interface 520 (FIG. 5) would perform the buffering functions otherwise provided by the buffer 820.

The optical probe 810 of FIG. 8 is advantageously used to measure perfusion via pulse oximetry methods. The disclosed embodiment is configured to measure reflected light; embodiments measuring transmissivity are also possible. The light source 816 includes two LEDs, one red LED in the 600-750 nm range and an infrared LED in the 850-1000 nm range. To obtain a single measurement, the two LEDs are pulsed (preferably in sequence) and two corresponding measurements are obtained at the light sensor 818, a photodiode. The ratio of red reflectivity to infrared reflectivity is calculated (by the detection subsystem 522 or CPU 528). Preferably, multiple ratio measurements are obtained over the course of at least one heart beat to obtain a value for peak perfusion, typically by subtracting minimum values (baselines) from maximum values (maximum perfusion). The peak value is compared to a preprogrammed lookup table to obtain an oxygen saturation value; the contents of the lookup table would be routine to calculate for a practitioner of ordinary skill.

It will be noted that perfusion measurements obtained by the optical probe 810 are typically relevant only in comparison to previously obtained values or trends, as measurements may be affected over a long term by tissue growth and other physiological changes around the probe 810. As will be described in detail below, systems and methods according to the invention perform accordingly.

In an embodiment of the invention, the light source 816 is further operable to optically stimulate brain tissue, which may result in perfusion changes or other desired neurophysiological results. For purposes of measurement, however, it is preferable to operate the light source 816 with low amplitude, duration, and other characteristics that are unlikely to cause undesired effects.

Figure 9:
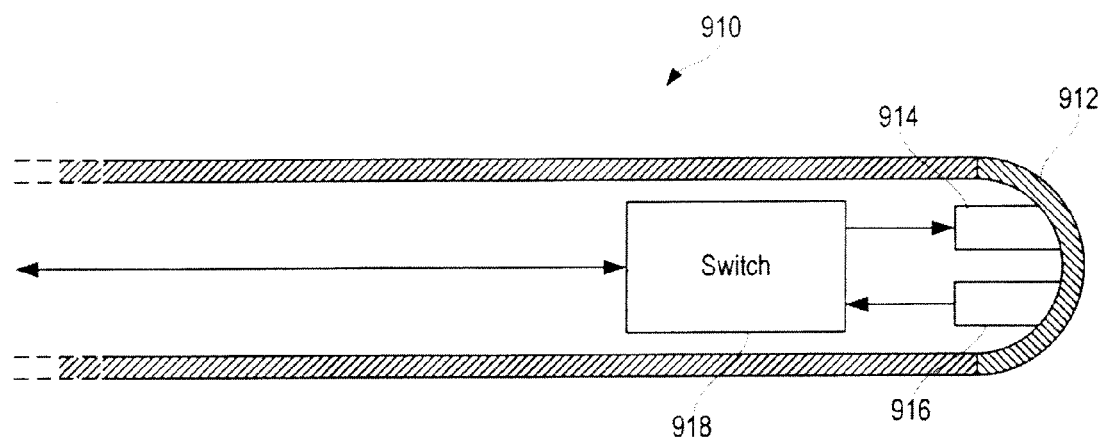
FIG. 9 is a schematic cutaway diagram of a thermographic sensing and stimulation probe according to the invention.

A thermal probe 910 is illustrated in FIG. 9; it is capable of measuring cerebral perfusion by thermographic means. The thermal probe 910 includes a thermally conductive distal tip 912 (the shape of which is as desired to reach a preferred target or region) coupled to a thermal energy source 914 (such as a Peltier junction or stack) and a temperature sensor 916 (in one embodiment, a temperature sensitive resistor). The thermal probe 910 is otherwise relatively thermally insulated. As shown, the thermal energy source 914 and the temperature sensor 916 are electrically coupled to a switch 918 facilitating the use of a single set of control wires, and as with the optical probe 810, the switch 918 may be omitted in favor of multiple connections. The switch 918 need not be as complex as the buffer 820 (FIG. 8), as thermography calls for temperature measurements to be obtained after thermal stimulation is applied; simultaneous operation of the thermal energy source 914 and the temperature sensor 916 is generally not required. The switch is advantageously operated via signals from the device 110.

Thermographic measurement of perfusion is generally accomplished by applying a caloric stimulus (via the thermal energy source 914), either hot or cold, and measuring the temperature over an interval thereafter to determine how quickly heat dissipates. Increased dissipation correlates with higher blood flow. Thermographic techniques, and their calibration, are well known to practitioners of ordinary skill. As with optical measurements, thermographic measurements of perfusion are most useful in a relative sense, compared to a previously measured baseline, and may be subject to long-term changes.

Thermal stimulation may also be performed by the probe 910 to modulate cerebral perfusion; generally, and increase in temperature will tend to increase blood flow in the region, and a decrease in temperature will lead to lower blood flow. Preferably, when measurements are to be made, smaller perturbances to temperature are preferred.

Thermographic probes as generally described herein are commercially available.

Figure 10:
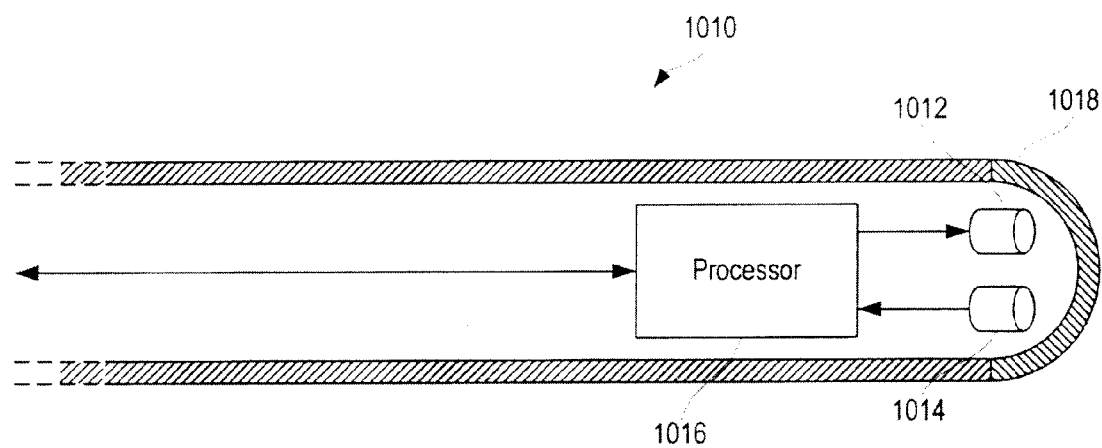
FIG. 10 is a schematic cutaway diagram of an ultrasonic sensing and stimulation probe according to the invention.

FIG. 10 illustrates an ultrasonic probe 1010, including an ultrasonic transmitter 1012, an ultrasonic receiver 1014, and a processor 1016 all behind a partially acoustically transparent distal probe tip 018. In the disclosed embodiment, the ultrasonic probe 1010 is adapted to measure perfusion via Doppler flowmetry, a technique well known in the art. The disclosed embodiment includes the Doppler processing in the probe via the processor 1016, though the calculations may also be performed on board the device 110.

The ultrasonic transmitter 1012 is, in the disclosed embodiment, a piezoelectric transducer configured to operate at a frequency greater than approximately 1 MHz. The ultrasonic receiver 1014 is adapted to receive at a range of similar and compatible frequencies. Pulsed measurements enable selection of measurement depth (e.g., the distance in front of the probe 1010 from which a measurement is taken).

Ultrasonic stimulation may also be performed by an ultrasonic probe 1010 according to the invention; ultrasonic stimulation generally operates to increase perfusion at the stimulation site.

Ultrasonic flow probes potentially suitable for use in connection with various embodiments of the present invention are commercially available. Regardless of the embodiment, when placing an ultrasonic probe, it is particularly important to avoid air bubbles and other gas pockets in front of the transducer, as such obstructions may confound measurements.

Figure 11:
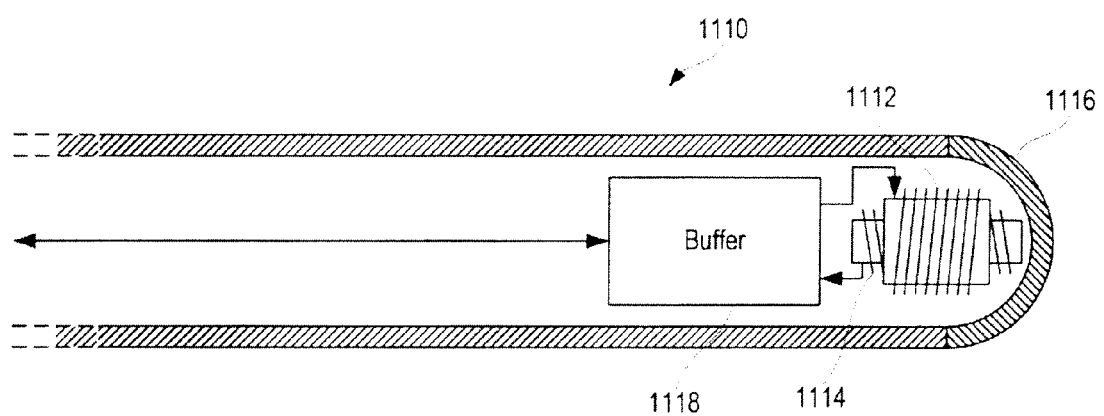
FIG. 11 is a schematic cutaway diagram of an electromagnetic sensing and stimulation probe according to the invention.

FIG. 11 illustrates an electromagnetic probe 1110 according to the invention, which includes a first field generating coil 1112 and a second sensing coil 1114 behind a magnetically permeable tip 116. As wraith the other probe embodiments, a buffer 1118 is provided to enable a single set of control wires to be used and to offload some processing from the device 110.

The electromagnetic probe 1110 is capable of measuring blood flow volume and rate by applying a magnetic field with the first field generating coil 1112 and measuring changes in electrical potential created across the second sensing coil 1114 caused by the movement of ferromagnetic or polarized objects, in the present case blood cells, within the field. The general technique of electromagnetic flowmetry is well known.

Localized electromagnetic stimulation may also be applied by the electromagnetic probe 1110. Depolarization potentially caused by a magnetic field may have therapeutic effects at or near a seizure focus or at a functionally relevant brain structure, or the magnetic field may be manipulated to affect perfusion in a desired manner according to the invention. In an embodiment of the invention, transcranial magnetic stimulation may be applied at a global scale (e.g., through the interface device 324, FIG. 3) to accomplish similar results.

Figure 12:
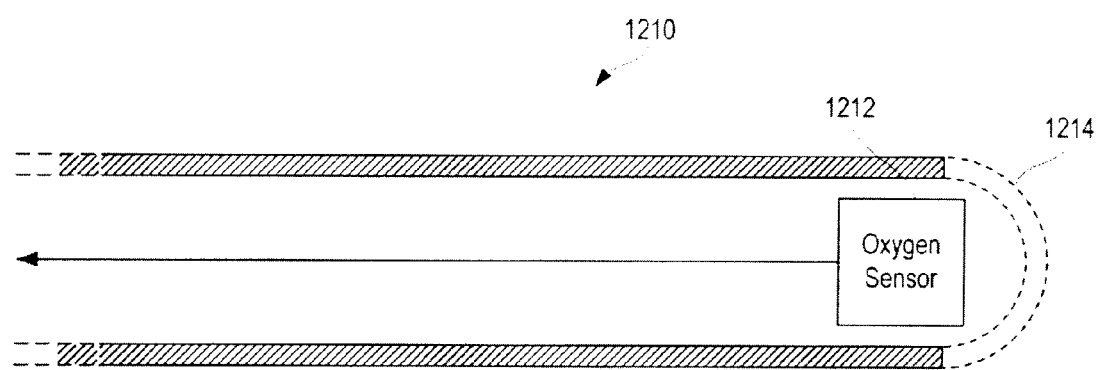
FIG. 12 is a schematic cutaway diagram of an electrochemical sensing probe according to the invention.

FIG. 12 illustrates an electrochemical oxygen probe 1210, which includes an oxygen sensor 1212 disposed behind a permeable tip 1214 or membrane. There are three common types of dissolved oxygen sensing probes: polarographic sensors, galvanic sensors, and optical fluorescence sensors, any of which may be adapted to serve the purposes of the invention to the extent they are biocompatible for long-term implant purposes. Dissolved oxygen levels correlate positively with perfusion levels, and may be used by systems and methods according to the invention to measure blood flow. The disclosed oxygen probe 1210 is not adapted to perform stimulation.

Other types of electrochemical sensing probes may also be used in this application, such as those detecting the presence of lactate in the neural tissue. These chemical markers may also be indicators of abnormal metabolism and perfusion levels.

Figure 13:
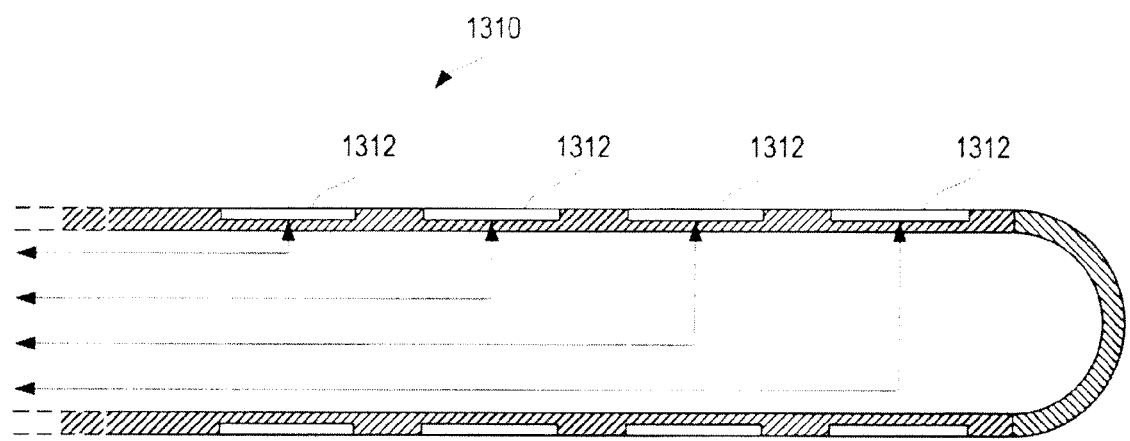
FIG. 13 is a schematic cutaway diagram of an electrical sensing and stimulation lead according to the invention.

A lead 1310 with four ring electrodes 1312 is illustrated in FIG. 13. In addition to traditional electrographic sensing and electrical stimulation as described above, the lead 1310 can be used to measure local perfusion by electrical impedance plethysmography. Accordingly, low current and short pulses of electrical stimulation (to avoid undesired depolarization and electrographic interference artifacts, and to improve battery life) are applied and impedance is measured between a pair of electrodes 1312 on the lead 1310.

As with other measurements described herein, electrical impedance plethysmography is advantageously used in a relative comparison to baseline measurements, rather than as an absolute value. Further, compensation for routine heart-rhythm-based variations (by taking average or peak values over several measurements) is also deemed ads advantageous.

With a sufficient number of electrodes disposed around a target site, it is possible to use a series of impedance measurements between different sets of electrodes to reconstruct a tomographic image of blood flow; techniques for accomplishing electrical impedance tomography are well known. In a presently preferred embodiment of the invention, data is collected for tomographic measurements by the device 110 and transferred to the programmer 312 or other external apparatus, where the intensive computations needed to reconstruct visualizations are more feasibly carried out.

Figure 14:
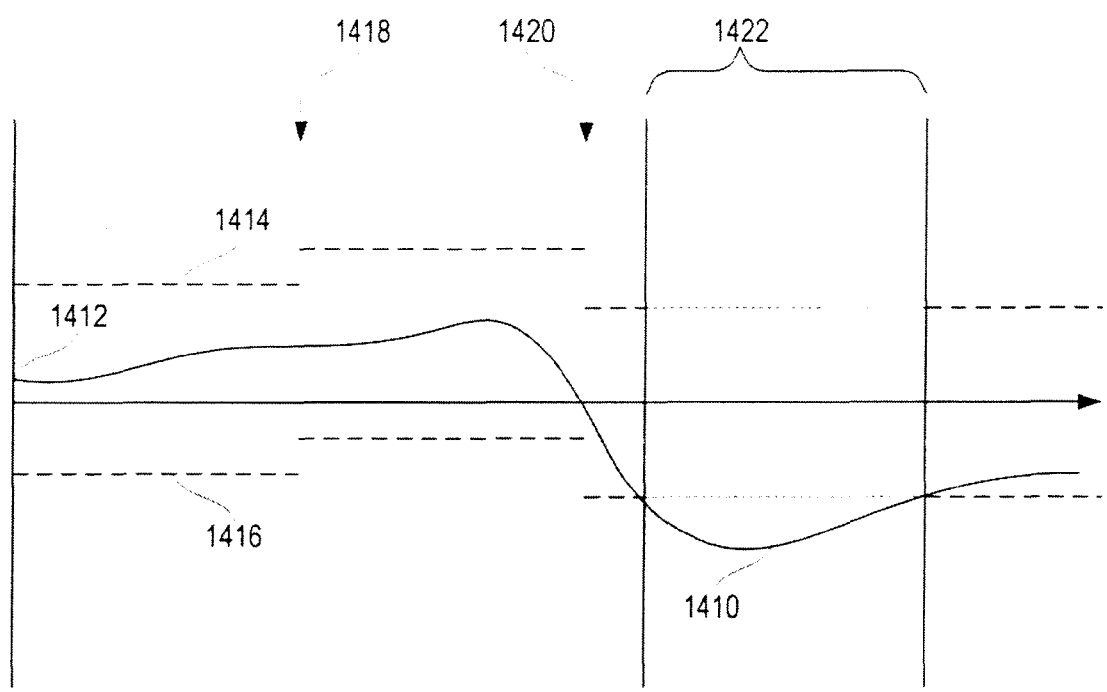
FIG. 14 is an exemplary graph of cerebral blood flow measurements in relation to thresholds calculated according to the invention.

FIG. 14 illustrates a sample hypothetical graph of cerebral perfusion measurements. At its start 1412, a perfusion curve 1410 (not illustrated to any particular scale) is approximately centered between an upper threshold 1414 and a lower threshold 1416. The perfusion curve 1410 shows gradually increasing perfusion up to a first time 1418, at which the thresholds 1414 and 1416 are recalculated to accommodate long-term trending. The thresholds 1414 and 1416 are recalculated again at a second time 1420, and shortly thereafter at a third time 1422 the curve 1410 starts to drop below the lower threshold 1416. This drop below an adjusted threshold indicates, in an exemplary system or method according to the invention, an undesired drop in perfusion, indicating that a therapeutic action should be taken as discussed in connection with the flow chart of FIG. 15 below. In an embodiment of the invention, cerebral blood flow is directly modulated (by means described herein) to increase it above the threshold 1416, or other actions may be taken alone or in conjunction with blood flow modulation.

During the time period 1422 the curve 1410 is below the lower threshold 1416, the thresholds 1414 and 1416 are not recalculated. Thresholds are readjusted periodically (in a preferred embodiment of the device 110, a selectable number of seconds).

Figure 15:
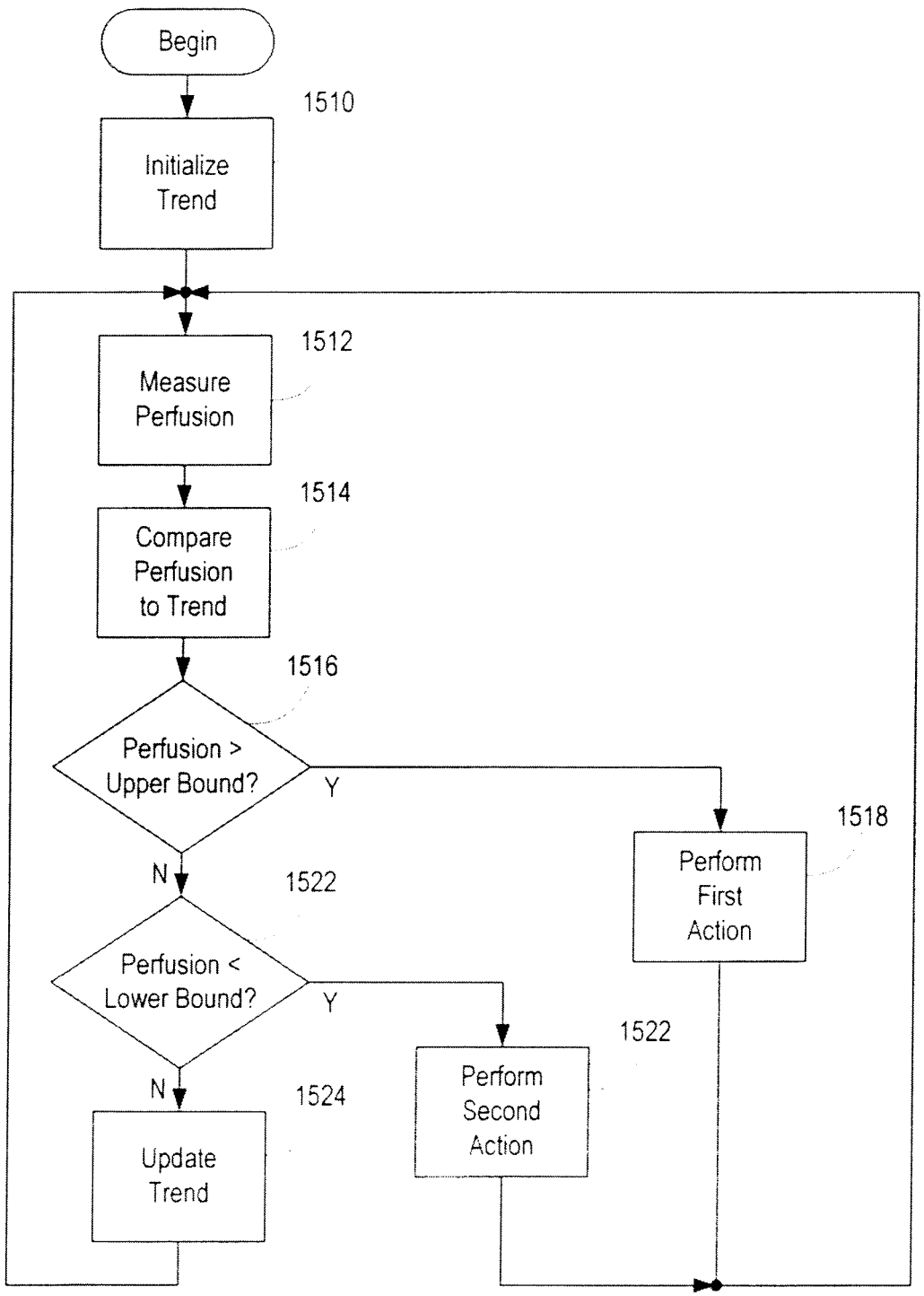
FIG. 15 is a flow chart illustrating an exemplary sequence of steps performed in measuring cerebral blood flow and responding to treat epilepsy and other disorders according to the invention.

A method according to the invention is performed as illustrated in FIG. 15, by initializing a perfusion trend value (step 1510). This is performed by performing an initial perfusion measurement (or average of a sequence of measurements) and storing it in a trend variable.

Perfusion at a desired site is then measured (step 1512) by one of the methods described herein or any other applicable technique. The measurement is then compared (step 1514) to the previously calculated trend. If the perfusion measurement exceeds an upper bound (step 1516), namely the trend value plus an upper threshold value (or in an alternative embodiment, the trend value multiplied by an upper threshold factor generally greater than one), then a first action is performed (step 1518). This condition, when the perfusion exceeds a threshold, indicates hyperperfusion that may be an undesired or pathological condition, or at least an indication that conditions are out of equilibrium and require therapeutic intervention.

To treat hyperperfusion, electrical (or other) stimulation according to the invention may be applied to the patient's caudate nucleus; stimulating other anatomical targets may also serve to decrease perfusion. An audio alert, somatosensory stimulation, or other indication may also be provided to the patient or a caregiver via the device 110 or its communication subsystem 530 (FIG. 5).

If the perfusion measurement exceeds (i.e., is lower than) a lower bound (step 1520), namely the trend value minus a lower threshold value (or in an alternative embodiment, the trend value multiplied by a lower threshold factor generally less than one), then a second action is performed (step 1522).

This condition, when the perfusion is lower than a threshold, indicates hypoperfusion that may be an undesired or pathological condition suggestive of an imminent epileptic seizure. Hypoperfusion may be treated by applying electrical (or other) stimulation at or near the site where the hypoperfusion was observed, frequently a seizure focus. As with hyperperfusion, feedback may be provided to the patient or caregiver. Alternatively, external therapy (such as transcranial magnetic stimulation) may be applied, either automatically or manually (based on an indication).

As set forth above, for either hyperperfusion or hypoperfusion, stimulation of a variety of anatomical targets may be performed according to the invention to produce beneficial changes in cortical blood flows to treat neurological disorders. Specifically, but not by way of limitation, potential stimulation targets include cortex of the brain (including specialized structures such as the hippocampus), white matter, basal ganglia (including the caudate nucleus), the brain stem, the spinal cord, the cerebellum or any of various cranial or peripheral nerves including the vagus nerve. Somatosensory stimulation (including sound, vision, and touch) may be suitable in some circumstances, particularly for acute therapy.

If the perfusion is within bounds, the trend variable is updated (step 1524), preferably periodically as described above. The method proceeds by repeating a perfusion measurement (step 1512) and continuing.

The actions taken need not be therapeutic in nature; they may serve other purposes. In one embodiment of the invention, the device 110 is essentially a seizure counter adapted to identify and collect information about periods of abnormal perfusion for later retrieval.

The flow chart of FIG. 15 is not an exclusive description of methods performed by a system according to the invention. Rather, it describes a single aspect of a single embodiment of a system according to the invention for observing blood flow and taking action in response to changes. This method may be performed in conjunction with, or in parallel with, other methods generally performed by implantable devices and implantable neurostimulators specifically. In particular, cerebral blood flow management may be considered a useful adjunctive therapy for an implanted responsive neurostimulator such as that described in detail in U.S. Pat. No. 6,810,285, referenced above, that is also capable of applying pulsatile electrical stimulation in response to detected abnormal electrographic activity.

One possible clinical scenario is as follows. Consider a patient in which hypo-perfusion is exhibited on one side of the brain where the patient's epileptiform activity originates. In the contralateral side, perfusion may be normal. This is considered to be a likely scenario, though by no means the only possible scenario. Some time before an epileptic seizure is likely to occur, perfusion starts to rise in the epileptic hemisphere, and plunges abruptly in the contralateral hemisphere just prior to the seizure. In this scenario, two parallel courses of the flow illustrated in FIG. 15 are contemplated, each one measuring perfusion in an area of interest in opposite hemispheres.

Interictally, while perfusion is low in the epileptic (hypoperfused) hemisphere, a system according to the invention is programmed to deliver electrical stimulation to increase perfusion and normalize the system. Each burst of stimulation tends to have a short-term effect. Stimulation may be provided intermittently but regularly, while perfusion is monitored. If perfusion rises beyond the amount caused by interictal stimulation, and especially if it is accompanied by a drop in perfusion in the contralateral hemisphere, then seizure activity may be anticipated. Accordingly, if the stimulation strategy is altered in light of the changed brain state, and an alternative course of therapy is initiated, which may include some or all the following: (1) stimulation of the caudate nucleus to decrease excitability in the epileptic hemisphere; (2) stimulation of the contralateral cortex to increase perfusion there; and (3) therapeutic electrical stimulation to reduce the likelihood of seizure activity. If ictal electrographic activity is then also observed in a system according to the invention, further actions may also be taken. Different actions may also be taken depending on whether the patient is asleep or awake (as potentially indicated by electrographic activity) or based on other measures of level of arousal or activity, as these factors may also tend to affect perfusion.

It should be observed that while the foregoing detailed description of various embodiments of the present invention is set forth in some detail, the invention is not limited to those details and an implantable medical device or system made according to the invention can differ from the disclosed embodiments in numerous ways. In particular, it will be appreciated that embodiments of the present invention may be employed in many different applications to responsively treat epilepsy and other neurological disorders. It will be appreciated that the functions disclosed herein as being performed by hardware and software, respectively, may be performed differently in an alternative embodiment. It should be further noted that functional distinctions are made above for purposes of explanation and clarity structural distinctions in a system or method according to the invention may not be drawn along the same boundaries. Hence, the appropriate scope hereof is deemed to be in accordance with the claims as set forth below.

What is claimed is:

1. An implantable device for modulating cerebral blood flow in a human patient and configured to be implanted in the human patient, the device comprising:
    a therapy output adapted to receive a signal and deliver a corresponding stimulus to the patient's brain in response thereto, wherein the stimulus changes a characteristic of the patient's cerebral blood flow; and
    a therapy controller configured to automatically generate the signal representative of the stimulus based on measured cerebral blood flow and a determined cerebral blood flow trend and communicate the signal to the therapy output.

2. The implantable device of claim 1, wherein the stimulus is adapted to increase perfusion.

3. The implantable device of claim 1, wherein the stimulus is adapted to decrease perfusion.

4. The implantable device of claim 1, wherein the therapy output comprises an optical stimulator.

5. The implantable device of claim 1, wherein the therapy output comprises a thermal stimulator for heating or cooling.

6. The implantable device of claim 1, wherein the therapy output comprises an electromagnetic stimulator.

7. The implantable device of claim 1, wherein the therapy output comprises an ultrasonic transducer.

8. The implantable device of claim 1, wherein the therapy output comprises a stimulation electrode.

9. The implantable device of claim 1, wherein the signal is generated intermittently and regularly.

10. The implantable device of claim 1, wherein the signal is generated in response to a detected change in a neurological condition.

11. An implantable device for modulating cerebral blood flow in a human patient and configured to be implanted in the human patient, the device comprising:

a therapy output adapted to receive a signal and deliver a corresponding stimulus to the patient's brain in response thereto, wherein the stimulus changes a characteristic of the patient's cerebral blood flow; and a therapy controller configured to automatically generate the signal representative of the stimulus based on measured cerebral blood flow and a determined cerebral blood flow trend and communicate the signal to the therapy output, the therapy controller further adapted to initialize a cerebral blood flow trend value by performing a sequence of perfusion measurements and taking the average of the sequence and storing the average in a memory in a trend variable as a trend value.

12. The implantable device of claim 11, the therapy controller further configured to compare the measured cerebral blood flow to the trend value and to determine whether to initiate an action based on the comparison.

13. The implantable device of claim 12, the therapy controller further configured to determine whether to initiate an action based on the comparison by comparing the measured cerebral blood flow to the trend value added to a threshold value.

14. The implantable device of claim 13 wherein the threshold value is either a positive or a negative value.

15. The implantable device of claim 12, the therapy controller further configured to determine whether to initiate an action based on the comparison by comparing the measured cerebral blood flow to the trend value multiplied by a threshold factor.

16. The implantable device of claim 15 wherein the threshold factor is either a positive or a negative value.

17. The implantable device of claim 15 wherein the threshold factor corresponds to a number greater than one.

18. The implantable device of claim 11 wherein the memory is located in the implantable device.

19. The implantable device of claim 11 wherein the memory is not located in the implantable device.

* * * * *